US006446631B1

(12) United States Patent
Hagiwara

(10) Patent No.: US 6,446,631 B1

(45) Date of Patent: Sep. 10, 2002

(54) ORAL STIMULATOR

(76) Inventor: Hidenori Hagiwara, 9-17, Ohoka 3-chome, Minami-ku, Yokohama-shi, Kanagawa-ken (JP)

( * ) Notice: Subject to any disclaimer, the term of this patent is extended or adjusted under 35 U.S.C. 154(b) by 0 days.

(21) Appl. No.: 09/486,265

(22) PCT Filed: Aug. 13, 1998

(86) PCT No.: PCT/JP98/03610

§ 371 (c)(1), (2), (4) Date: Feb. 22, 2000

(87) PCT Pub. No.: WO99/09930

PCT Pub. Date: Mar. 4, 1999

(30) Foreign Application Priority Data

| | | |
|---|---|---|
| Aug. 22, 1997 | (JP) | 9-7483 |
| Oct. 21, 1997 | (JP) | 9-288312 |
| Feb. 10, 1998 | (JP) | 10-28755 |

(51) Int. Cl.[7] .................... A61F 5/56

(52) U.S. Cl. .................... 128/848; 128/859

(58) Field of Search .................... 128/848, 859–861; 602/902

(56) References Cited

U.S. PATENT DOCUMENTS

| | | | | |
|---|---|---|---|---|
| 1,302,004 A | * 4/1919 | Brown | 128/861 |
| 2,694,397 A | * 11/1954 | Herms | 128/861 |
| 4,867,147 A | * 9/1989 | Davis | 128/859 |
| 5,823,193 A | * 10/1998 | Singer | 128/848 |

* cited by examiner

*Primary Examiner*—Michael A. Brown

(74) *Attorney, Agent, or Firm*—Bierman, Muserlian and Lucas

(57) ABSTRACT

In order to easily and effectively press and stimulate an affected part to be pressed for treatment without depending on a specialist, an oral stimulator comprises a mounting portion (11) which is to be mounted on at least a part of the teeth and a pressing portion (12) which is integrally fixed to the mounting portion (11) so that it can press the affected part from inside the mouth in a state where the mounting portion (11) is mounted on the teeth.

16 Claims, 8 Drawing Sheets

ORAL STIMULATOR

FIELD OF THE INVENTION

This invention relates to an oral stimulator for pressing various points, a jaw articulation, or the like from inside the mouth for various treatment.

BACKGROUND OF THE INVENTION

In oriental medicine, there has been known that there are a plurality of points on the face as shown in FIG. 18 and the patient can be recovered from various indisposition by stimulating a particular point with a needle or moxa.

For example, by stimulating points C called “Geikou” at the middles between the middle points of the outer peripheries A, A of the nosewings and the nasolabial folds (folds on opposite sides of the nose), B, B, olfaction abnormalities, nasal congestion and the like can be cured. Symptoms of nasitis can be cured by stimulating points D called “Biryu” at the middle points of straight lines joining the nostril, the nasal septum columella and the nosewing or points E called “Sanshou” at the middle points of the nasolabial folds below the “Geikow” points. Further by stimulating points F called “Koryou” at 3 cm outward from the nosewings, symptoms of nasal catarrh, trigeminal neuralgia and facial paralysis can be lightened.

Further, as shown in FIG. 19, there are points inside the mouth. In the oriental medicine, there is treatment in which the points in the mouth are pricked with a needle or with a fleam to cause bleeding at the points. For example, when you roll upward the tip of the tongue and nip the tongue between your upper and lower front teeth, you can find two veins on the back side of the tongue. By stimulating a point G called “Kinshin” on the left vein or a point H called “Gyokueki” on the right vein, swelling or pain of the tongue or symptom of aphasia can be lightened.

When you open the mouth wide with your right and left hands applied to your right and left jaw articulations, you can feel parts which move largely. When you suffer from an articular disease at the jaw or symptom of bruxism, the inside of the parts is stiff and there is observed strain of muscles. In such a case, by pressing the jaw articulation rearward upward from behind the root of the upper and lower teeth with a finger, strain of the affected part is lightened, whereby various feelings of physical disorder such as a feeling that the jaws are wobbly, a feeling of oppression and feeling a pain when biting strongly can be lightened.

Since it is impossible to successfully press the “Geikou” point, “Koryou” point and the like from the surface of the face and at the same time it is impossible to press them long from the surface of the face, conventionally stimulation of such a point has to depend on a specialist. Similarly it is impossible to press the jaw articulation with a finger for a long time from the inside of the mouth, stimulation of the jaw articulation conventionally has to depend on a specialist. Further, since the “Kinshin” point and the “Gyokueki” point are sensitive to pain, stimulation of the “Kinshin” point and the “Gyokueki” point with a needle has not been performed in the past.

In view of the foregoing observations and description, the primary object of the present invention is to provide an oral stimulator which makes it feasible to easily stimulate, without depending on a specialist, various points or the jaw articulation without involving a sharp pain so that various remedial values can be expected.

DISCLOSURE OF THE INVENTION

The oral stimulator in accordance with the present invention comprises a mounting portion which is mounted on at least a part of the teeth and a pressing portion which is integrally fixed to the mounting portion so that it can press an affected part to be pressed for treatment from inside the mouth in a state where the mounting portion is mounted on the teeth.

The affected part to be pressed for treatment is a part such as a point, an articulation and the like pressing on which is expected to be effective for treatment.

In one embodiment of the present invention, the mounting portion is shaped to be mounted on at least a part of the upper teeth and the pressing portion is shaped to be able to press upward the “Geikou” point, the “Biryu” point, the “Sanshou” point or the “Koryou” point from inside the upper lip or the cheek. In another embodiment of the present invention, the mounting portion is shaped to be mounted on at least a part of the lower teeth and the pressing portion is shaped to be able to press upward the “Kinshin” point or the “Gyokueki” point from inside the lower jaw. The pressing portion may be shaped to be able to press points other than those described above. In still another embodiment of the present invention, the mounting portion is shaped to be mounted on at least a part of the upper teeth and the pressing portion is shaped to be able to press upward the jaw articulation from inside the mouth.

The mounting portion may be shaped to be mounted on only a front portion of the upper teeth or only a back portion of the lower teeth. In this case, it is preferred that the mounting portion be able to be softened by hot water so that it can be folded to conform to the shape of the teeth.

The mounting portion may be shaped like a mouthpiece. The term “mouthpiece” as used herein means a mouthpiece which is used to protect the teeth and/or the inside of the mouth in contact sports such as football, boxing or the like and is mounted on the whole upper teeth or the whole lower teeth.

Though the mounting portion and the pressing portion can be formed by one-piece molding, they may be separately formed of heat-resistant materials and the pressing portion may be fixed to the mounting portion at its base portion.

The tip of the pressing portion may be shaped like a ball. A permanent magnet or a mineral (e.g., amethyst) may be attached to the tip of the pressing portion.

This invention has found the fact that olfaction abnormalities, nasal catarrh and the like can be cured by pressing points on the face such as “Geikou” and “Koryou” even from inside the mouth, that pressing can be employed to stimulate points such as “Kinshin” which are sensitive to pain, and that the effect of movement massage can be obtained by pressing the affected part with a tool and has invented an oral stimulator for this purpose.

Since the oral stimulator of this invention comprises a pressing portion which can press an affected part and is integrally fixed to a mounting portion, anybody can easily and effectively stimulate from inside the mouth an affected part near the mouth for the purpose of various remedial values by only mounting the oral stimulator of this invention on the teeth. Further the oral stimulator of this invention is preferable also from the viewpoint of beauty since it does not leave no traces of treatment on the face unlike moxa treatment.

When the pressing portion is shaped to be able to press upward the “Geikou” point from inside the upper lip, olfaction abnormalities, symptoms of running nose due to cold or hay fever, nasal congestion and the like can be cured. It is especially effective to hay fever.

When the pressing portion is shaped to be able to press the "Biryu" point or the "Sanshou" point, symptoms of nasitis can be lightened, and when the pressing portion is shaped to be able to press the "Koryou" point, symptoms of nasal catarrh, trigeminal neuralgia and facial paralysis can be lightened. When the pressing portion is shaped to be able to press the "Kinshin" point or the "Gyokueki" point, swelling or pain of the tongue or symptom of aphasia can be lightened without causing sharp pain and without insanitary affect. The pressing portion may be shaped to press other points in the mouth. In this case, different remedial values can be effected according to the points to be pressed.

When the pressing portion is shaped to be able to press the jaw articulation behind the root of the upper and lower teeth, anybody can easily and effectively press the jaw articulation to obtain a finger-pressure cure effect and continue movement massage for a long time as will be described later, whereby strain of the affected part is lightened and various feelings of physical disorder can be lightened.

When the mounting portion is shaped to be mounted on only a front portion of the upper teeth or only a back portion of the lower teeth, the overall size of the oral stimulator of the present invention can be very small and accordingly the sense of incompatibility which one feels when the oral stimulator is mounted in his or her mouth can be minimized. Especially when the mounting portion and the pressing portion are formed by one-piece molding, production of the oral stimulator is facilitated. When the mounting portion is able to be softened by hot water so that it can be folded to conform to the shape of the teeth, the mounting portion can be deformed to conform to a front portion of the upper teeth or a back portion of the lower teeth of anybody, the oral stimulator can be stably mounted in the mouth.

When the mounting portion is like a mouthpiece, the oral stimulator can be supported by the whole jaws and can be more stably supported, and at the same time, the strength of stimulation can be controlled by controlling the manner of setting the upper and lower teeth and/or the manner of getting in and out the tongue.

When the tip of the pressing portion is shaped like a ball, stimulation can be lightened, when a permanent magnet is attached to the tip of the pressing portion, the remedial values can be enhanced and when a mineral (e.g., amethyst) is attached to the tip of the pressing portion, the remedial values can be enhanced by a wave effect of the mineral.

DESCRIPTION OF THE PREFERRED EMBODIMENTS

Figure 1A:
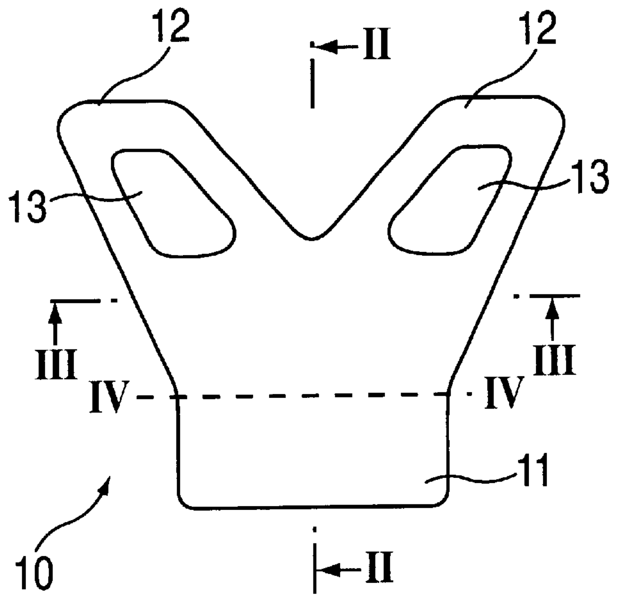
FIG. 1*a* is a front view showing an oral stimulator in accordance with a first embodiment of the present invention.
Figure 1B:
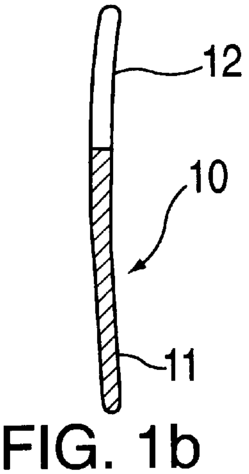
FIG. 1*b* is a cross-sectional view taken along line II—II in FIG. 1*a*.
Figure 1C:
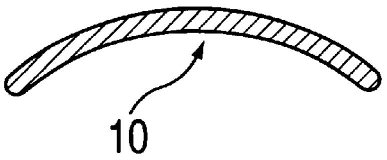
FIG. 1*c* is a cross-sectional view taken along line III—III in FIG. 1*a*.

Embodiments of the present invention will be described in detail with reference to the drawings, hereinbelow.

FIGS. 1*a* to 1*d* are views showing an oral stimulator in accordance with a first embodiment of the present invention.

The oral stimulator 10 of this embodiment comprises a curved plate member provided with a mounting portion 11 to be mounted on a front portion of the upper teeth and a pair of pressing portions 12 which extend obliquely upward outward from the upper edge of the mounting portion 11, and is formed by one-piece molding of a plastic material whose softening point is lower than a highest temperature which the mouth cavity withstands and higher than normal temperatures inside the mouth. The pressing portions 12 are spaced from each other in the transverse direction of the oral stimulator 10 so that the distance between the centers of the tip portions of the respective pressing portions 12 is about 40 mm. Each of the pressing portions 12 is provided with opening 13 for increasing flexibility of the pressing portion 12. The oral stimulator 10 is about 56 mm in the maximum size as measured in the transverse direction, about 45 mm in the maximum size as measured in the vertical direction, and about 2 mm in thickness.

Figure 1D:
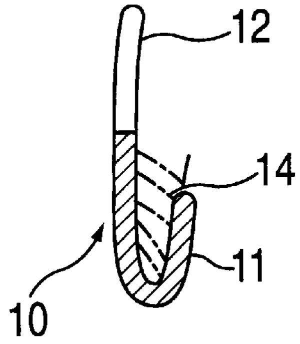
FIG. 1*d* is a cross-sectional view taken along line II—II in FIG. 1*a* showing a state where the mounting portion is folded along the broken line IV—IV in FIG. 1*a* to conform to the upper teeth.
Figure 2:
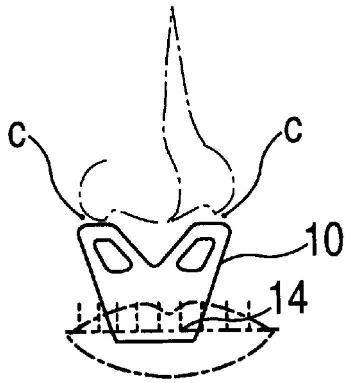
FIG. 2 is a schematic front view showing a mounted state of the oral stimulator of FIG. 1.
Figure 3:
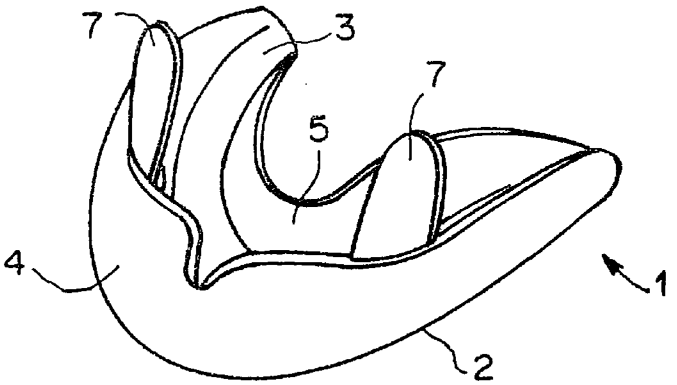
FIG. 3 is a perspective view showing an oral stimulator in accordance with a second embodiment of the present invention.
Figure 4:
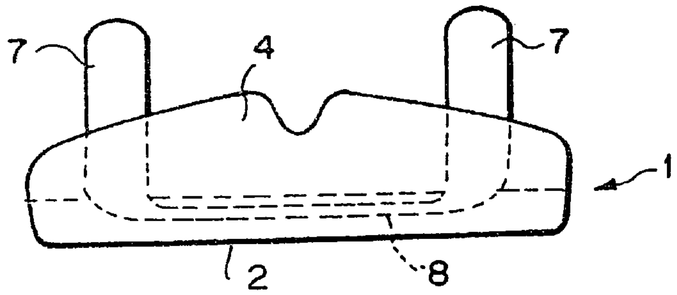
FIG. 4 is a front view of the oral stimulator shown in FIG. 3.
Figure 5:
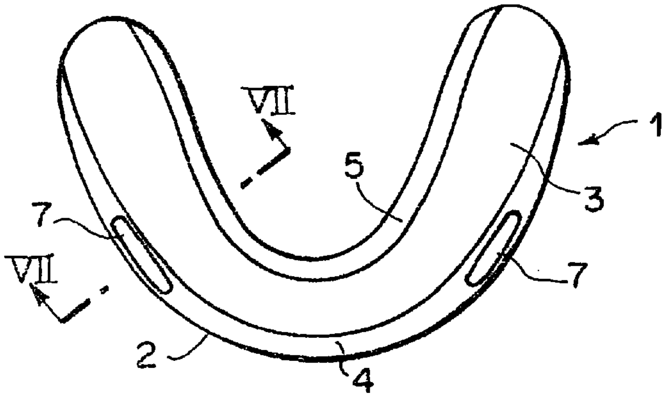
FIG. 5 is a plan view of the oral stimulator shown in FIG. 3.
Figure 6:
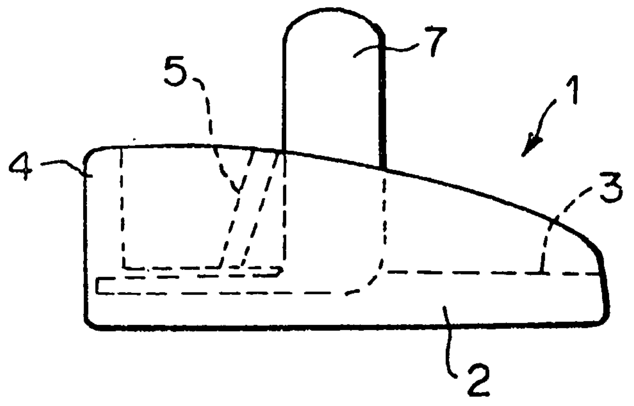
FIG. 6 is a side view of the oral stimulator shown in FIG. 3.
Figure 7:
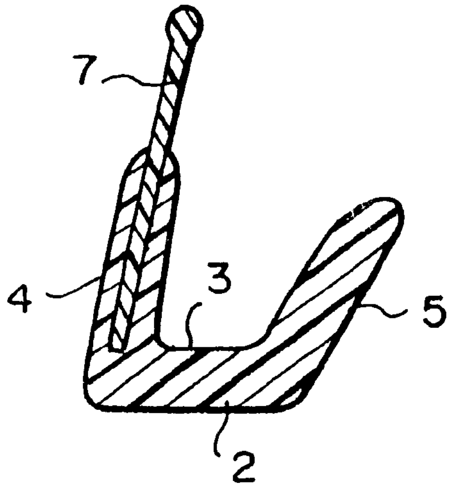
FIG. 7 is an enlarged cross-sectional view taken along line VII—VII in FIG. 5.

The oral stimulator 10 is dipped in hot water at about 80° C. and softened. Then the oral stimulator 10 is folded inward like U along line IV—IV in FIG. 1*a* to conform to the shape of a front portion of the upper teeth 14 as shown in FIG. 1*d* and is brought into a close contact with the front portion of the upper teeth 14. Thereafter the oral stimulator 1 is once removed from the mouth and dipped into cool water to solidify the mounting portion 11 and then mounted on the front portion of the upper teeth 14.

The oral stimulator 10 of this embodiment is arranged so that the tips of the pressing portions 12 press upward the "Geikou" points C, C from inside the upper lip in a state where the mounting portion 11 is mounted on the front portion of the upper teeth 14.

In accordance with this embodiment, it becomes possible to stimulate the "Geikou" points with a very simple structure and the oral stimulator 10 of this embodiment is advantageous in that the sense of incompatibility which one feels when the oral stimulator 10 is mounted in his or her mouth is minimum. By mounting the oral stimulator 10 on the front portion of the upper teeth 14 when olfaction abnormalities occur, the nose keeps running due to cold or hay fever, or nasal congestion occurs, such a symptom can be cured.

FIGS. 3 to 8*a* and 8*b* show an oral stimulator in accordance with a second embodiment of the present invention.

The oral stimulator 1 of this embodiment is provided with a mounting portion 2 which is formed like a mouthpiece. The mounting portion 2 is like a horseshoe in the overall shape and is formed of a plastic material such as ethylene vinyl acetate whose softening point is lower than a highest temperature which the mouth cavity withstands and higher than normal temperatures inside the mouth. The mounting portion 2 is provided with an occlusal portion 3, and a front wall portion 4 and a rear wall portion 5 are formed integrally with the occlusal portion 3 respectively along outer and inner edges of the occlusal portion 3.

Figure 8A:
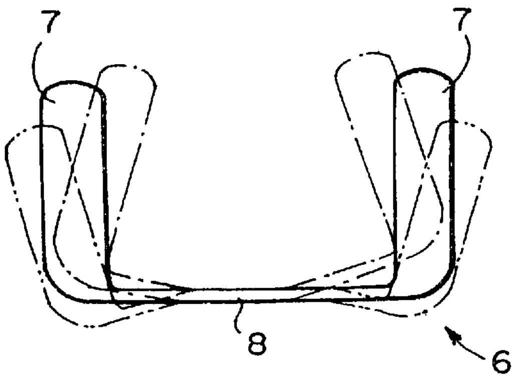
FIG. 8*a* is a front view of the insert member.
Figure 8B:
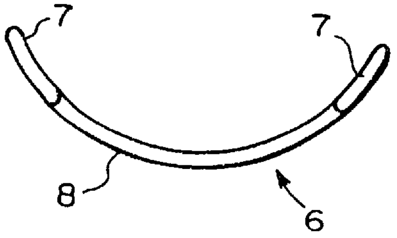
FIG. 8*b* is a plan view of the insert member.
Figure 9:
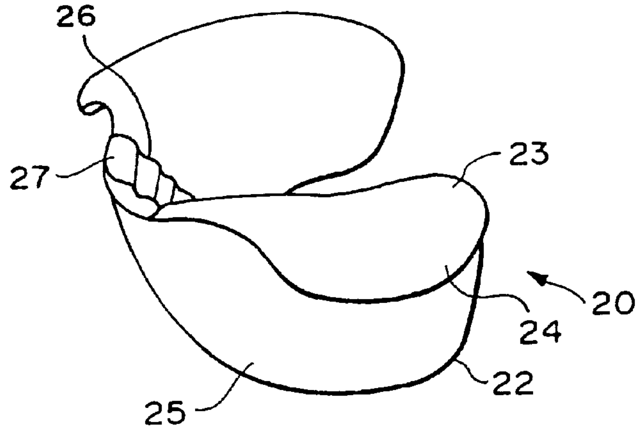
FIG. 9 is a perspective view showing an oral stimulator in accordance with a third embodiment of the present invention.
Figure 10:
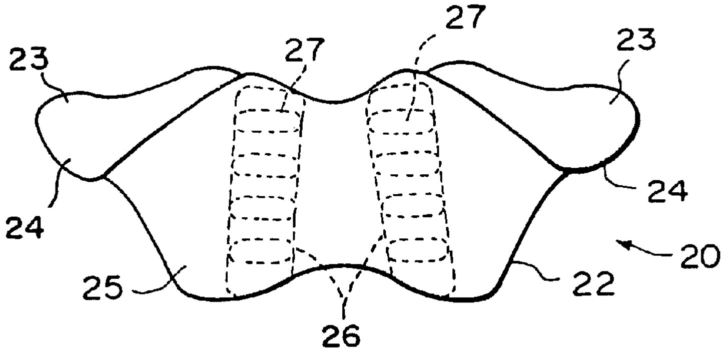
FIG. 10 is a front view of the oral stimulator shown in FIG. 9.
Figure 11:
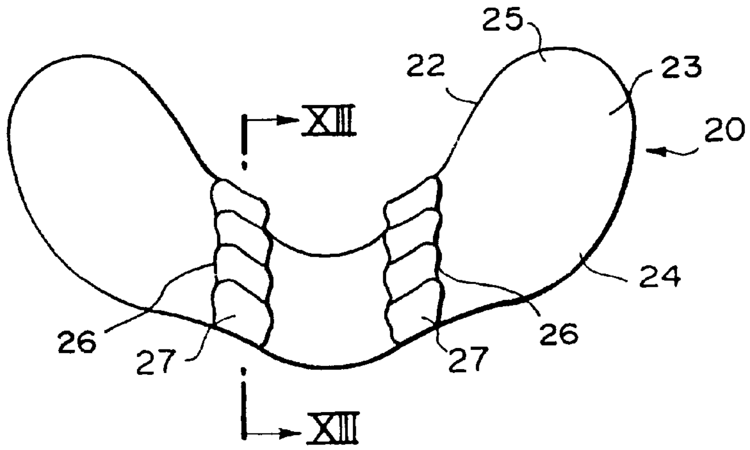
FIG. 11 is a plan view of the oral stimulator shown in FIG. 9.
Figure 12:
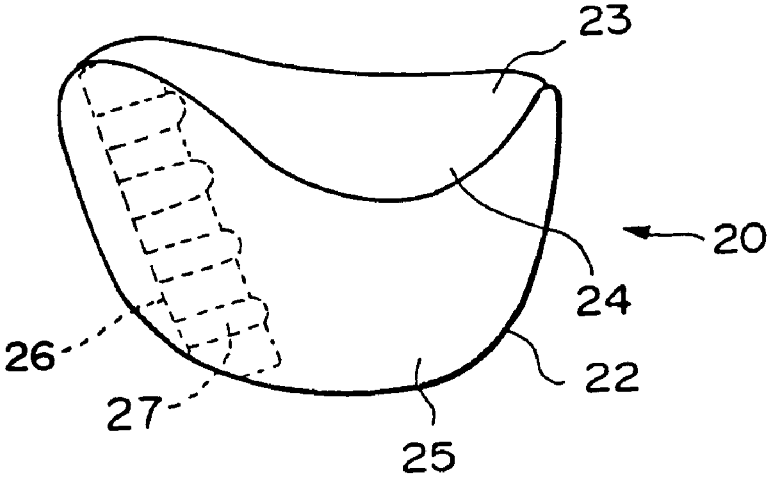
FIG. 12 is a side view of the oral stimulator shown in FIG. 9.

As shown in FIGS. 8*a* and 8*b*, an insert member 6 is mounted on the front wall portion 4. The insert member 6 comprises a pair of elongated pressing portions 7 and a curved connecting portion 8 which connects the lower end portions of the pressing portions 7. The pressing portions 7 and the connecting portion 8 are formed integrally with each other. The pressing portions 7 are spaced from each other by about 40 mm and extend in the vertical direction in a length of about 30 mm. The base portions of the pressing portions 7 together with the connecting portion 8 are embedded in the front wall portion 4, and only the upper portions of the pressing portions 7 project, symmetrically about the center line of the front wall portion 4, upward from the upper edge of the front wall portion 4 by about 15 mm. The tip of each of the pressing portions 7 forms a curved surface.

The insert member 6 is formed of a plastic material which is flexible and heat-resistant as shown in FIG. 8*a*.

The oral stimulator 1 of this embodiment is mounted in the mouth in the same manner as a known mouthpiece. That is, the oral stimulator 1 is first dipped in hot water at about 80° C. for about 10 seconds and softened. Then the mounting portion 2 is mounted on the upper jaw of a user. Thereafter the user bites the mounting portion 2 with his or her molar teeth to make teeth-marks and moves the tongue and/or the mouth to fit the mounting portion 2 on the teeth. Thereafter the user once takes the oral stimulator 1 out of the mouth and dips it in cool water, thereby solidifying the mounting portion 2. After the mounting portion 2 solidifies, the user mounts again the oral stimulator 1 in the mouth.

As in the first embodiment, by mounting the oral stimulator 1 in the mouth when olfaction abnormalities occur, the nose keeps running due to cold or hay fever, or nasal congestion occurs, the tips of the pressing portions 7 press the "Geikou" points C, C from inside the upper lip to stimulate the points and such a symptom can be cured.

Though, in the second embodiment, the tip of each pressing portion 7 is a curved surface, stimulation can be lightened when the tip is formed like a ball. Further, by embedding a permanent magnet or a mineral such as amethyst in the tip of the pressing portion 7, the remedial values can be increased.

FIGS. 9 to 13 show an oral stimulator in accordance with a third embodiment of the present invention.

The oral stimulator 20 of this embodiment is provided with a mounting portion 22 which is like a horseshoe in the overall shape and is integrally formed of a plastic material such as ethylene vinyl acetate whose softening point is lower than a highest temperature which the mouth cavity withstands and higher than normal temperatures inside the mouth. The mouthing portion 22 is provided with a rear wall portion 25 which is curved in a U-shape to conform to the array of the lower teeth and is to be positioned on the inner side of the lower teeth, a pair of occlusal portions 23 which extend laterally outward from the upper edge of the rear wall portion 25 at the left and right ends of the rear wall portion 25 (the portions corresponding to the left and right back sides of the lower teeth, and a pair of front wall portions 24 which extend downward from the outer edges of the respective occlusal portions 23.

Figure 13:
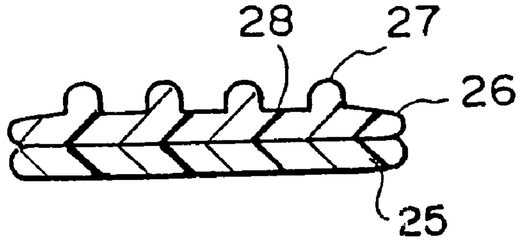
FIG. 13 is an enlarged cross-sectional view taken along lines XIII—XIII in FIG. 11.
Figure 14:
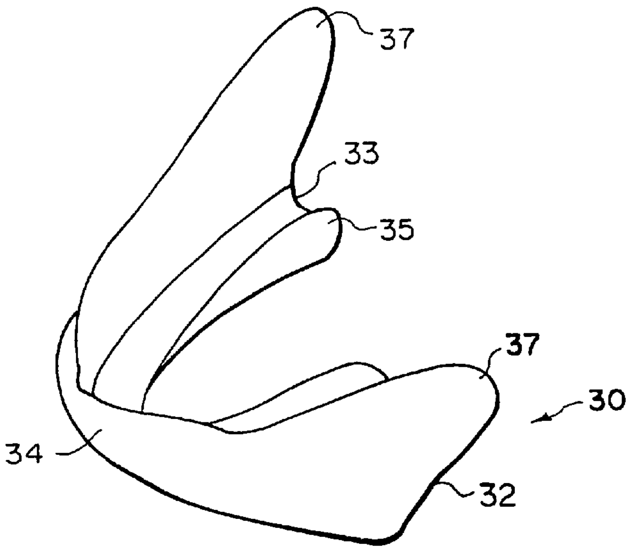
FIG. 14 is a perspective view showing an oral stimulator in accordance with a fourth embodiment of the present invention.
Figure 15:
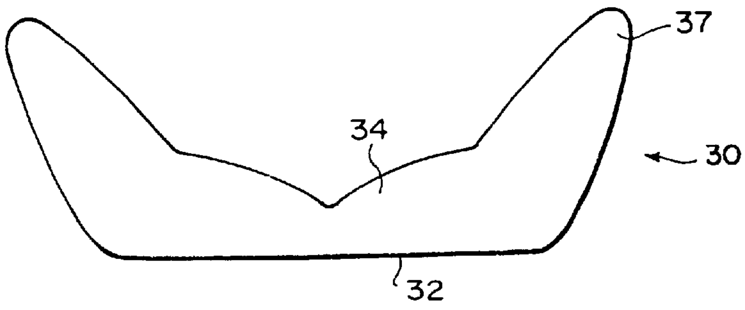
FIG. 15 is a front view of the oral stimulator shown in FIG. 14.
Figure 16:
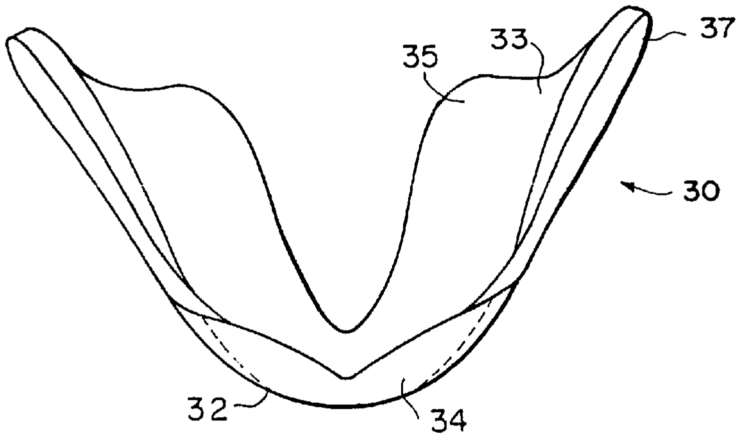
FIG. 16 is a plan view of the oral stimulator shown in FIG. 14.
Figure 17:
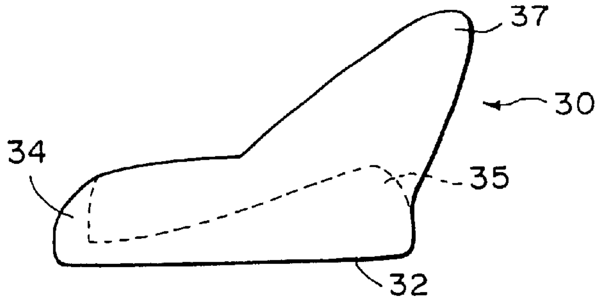
FIG. 17 is a side view of the oral stimulator shown in FIG. 14.
Figure 18:
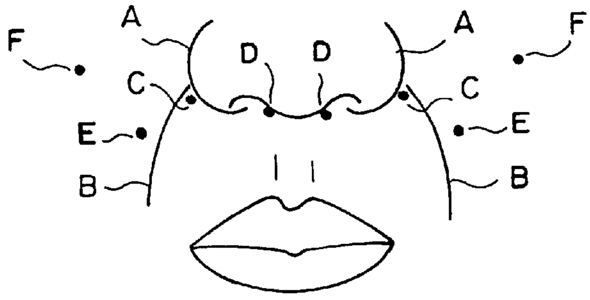
FIG. 18 is a view showing positions of points called "Geikou","Biryu","Sanshou" and "Koryou".
Figure 19:
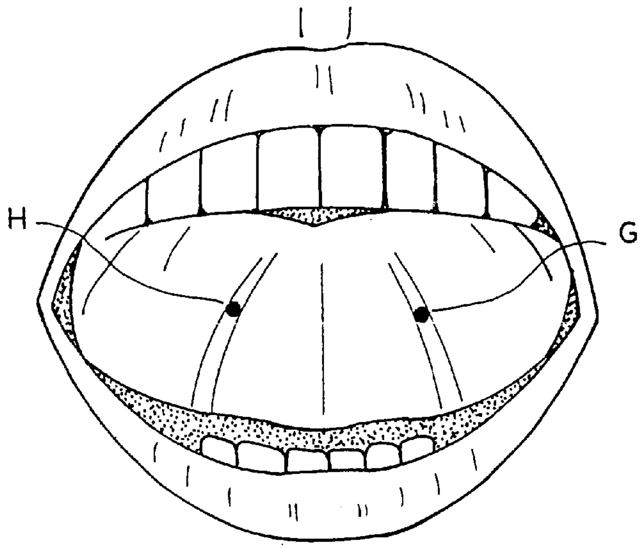
FIG. 19 is a view showing positions of points called "Kinshin" and "Gyokueki".

A pair of pressing portion mounting members 26 are integrally fixed to the rear side of a front portion of the rear wall portion 25. The pressing portion mounting member 26 comprises a plurality of pressing portions 27 which are in the form of projections about 3 mm high and a connection portion 28 which connects the lower end portions of the pressing portion 27 at intervals of about 5 mm. The pressing portions 27 and the connecting portion 28 are formed integrally with each other. As shown in FIG. 13, the tip of each pressing portion 27 forms like a curved surface. Though the pressing portion mounting member 26 is formed of a plastic material which is resilient, flexible and heat-resistant in this particular embodiment, it may be formed of other various materials such as a hard plastic.

By mounting the oral stimulator 20 of this embodiment on the lower teeth and doing exercise of getting in and out the tongue or rotating the tongue or rehabilitation on speech, the tips of the pressing members 27 press and stimulate the "Kinshin" point and the "Gyokueki" point, whereby swelling or pain of the tongue or symptom of aphasia can be lightened.

FIGS. 14 to 17 show an oral stimulator in accordance with a fourth embodiment of the present invention.

The oral stimulator 30 of this embodiment is provided with a mounting portion 32 which is formed like a mouthpiece to be mounted on the upper teeth. The mounting portion 32 is like a horseshoe in the overall shape and is formed of a plastic material such as ethylene vinyl acetate whose softening point is lower than a highest temperature which the mouth cavity withstands and higher than normal temperatures inside the mouth. The mounting portion 32 is provided with an occlusal portion 33, and a front wall portion 34 and a rear wall portion 35 are formed integrally with the occlusal portion 33 respectively along outer and inner edges of the occlusal portion 33.

A pair of pressing portions 37 about 30 mm high are mounted on the left and right end portions (rear end portions) of the front wall portion 34. The tip of each pressing portion 37 is formed like a curved surface. The pressing portion 37 is formed of a plastic material which is resilient, flexible and heat-resistant and may be either the same as or different from the material of the mounting portion 32.

By mounting the oral stimulator 30 of this embodiment on the upper teeth and biting strongly and weakly with the upper and lower teeth, the pressing portions 37 press and stimulate the jaw articulations, whereby movement massage is given to the muscle on the inner side of the jaw articulations to lighten strain of the muscle, and physical disorder at the jaw articulations can be lightened.

What is claimed is:

1. An oral stimulator comprising:

a mounting portion which is adapted to be mounted on at least a part of the teeth; and a pressing portion which is integrally fixed to the mounting portion, said pressing portion extending upwardly from said mounting portion a height such that when said mounting portion is mounted inside the mouth on the teeth said pressing portion presses upwardly against at least one pressure point selected from the group consisting of "Geikou","Biryu","Sanshou","Koryou", "Kinshin","jaw articulation",and "Gyokueki".

2. An oral stimulator as defined in claim 1 in which the mounting portion is shaped to be mounted on at least a part of the upper teeth and the pressing portion has a height and a shape to press upward the "Geikou" point, the "Biryu" point and or the "Sanshou" point from inside the upper lip.

3. An oral stimulator as defined in claim 2 in which the mounting portion is shaped to be mounted on only a front portion of the upper teeth.

4. An oral stimulator as defined in claim 1 in which the mounting portion is shaped to be mounted on at least a part of the upper teeth and the pressing portion has a height and a shape to press upward the "Koryou" point from inside the cheek.

5. An oral stimulator as defined in claim 3 in which the mounting portion is able to be softened by hot water so that it can be folded to conform to the shape of the teeth.

6. An oral stimulator as defined in claim 1 in which the mounting portion is shaped to be mounted on at least a part of the upper teeth and the pressing portion has a height and a shape to press upward the jaw articulation from inside the mouth.

7. An oral stimulator as defined in claim 1 in which the mounting portion is shaped to be mounted on at least a part of the lower teeth and the pressing portion has a height and a shape to press upward the "Kinshin" point or the "Gyokueki" point from inside the lower jaw.

8. An oral stimulator as defined in claim 1 in which the mounting portion is shaped like a mouthpiece.

9. An oral stimulator comprising:

a mounting portion which is adapted to be mounted on at least a part of the teeth; and a pressing portion integrally fixed at its base to the mounting portion, the pressing portion adapted to press upward, at least one pressure point selected from the group consisting of "Geikou", "Biryu", "Sanshou", "Koryou", "Kinshin", "jaw articulation", and "Gyokueki" from inside the mouth when said mounting portion is mounted on the teeth, the pressing portion being formed of a heat-resistant material.

10. An oral stimulator comprising:

a mounting portion which is shaped to be mounted on only a back portion of the lower teeth; and a pressing portion which is integrally fixed to the mounting portion, and is shaped to press upwardly the "Kinshin" point or the "Gyokueki"point from inside the lower jaw in a state where the mounting portion is mounted on the teeth.

11. An oral stimulator comprising:

a mounting portion which is adapted to be mounted on at least a part of the teeth; and a pressing portion which is integrally fixed to the mounting portion, and adapted to press an affected part to be pressed for treatment from inside the mouth in a state where the mounting portion is mounted on the teeth, and the pressing portion is formed of a heat-resistant material separately from the mounting portion and the pressing portion is fixed to the mounting portion at its base portion.

12. An oral stimulator comprising:

a mounting portion which is adapted to be mounted on at least a part of the teeth; and a pressing portion which is integrally fixed to the mounting portion, and adapted to press an affected part to be pressed for treatment from inside the mouth in a state where the mounting portion is mounted on the teeth, the pressing portion having a tip which is shaped like a ball.

13. An oral stimulator comprising:

a mounting portion which is adapted to be mounted on at least a part of the teeth; and a pressing portion which is integrally fixed to the mounting portion, and adapted to press an affected part to be pressed for treatment from inside the mouth in a state where the mounting portion is mounted on the teeth, wherein a permanent magnet is attached to the top of the pressing portion.

14. An oral stimulator comprising:

a mounting portion which is adapted to be mounted on at least a part of the teeth; and a pressing portion which is integrally fixed to the mounting portion, and adapted to press an affected part to be pressed for treatment from inside the mouth in a state where the mounting portion is mounted on the teeth, wherein a mineral is attached to the tip of the pressing portion.

15. An oral stimulator comprising:

a mounting portion which is adapted to be mounted on at least a part of the teeth; and a pressing portion which is integrally fixed to the mounting portion, said pressing portion having a V or U shape which extends upward from said mounting portion and a height such that when said mounting portion is mounted inside the mouth on the teeth the two ends of the V or U shape pressing portion press upwardly against at least one pressure point selected from the group consisting of Geikou, Biryu, Sanshou, and Koryou.

16. A method for stimulating at least pressure point selected from the group consisting of Geikou, Biryu, Sanshou, Koryou, Kinshin, jaw articulation, and Gyokueki comprising:

mounting an oral stimulator inside the mouth on the teeth, said oral stimulator comprising a mounting portion which is adapted to be mounted on at least a port of the teeth; and a pressing portion which is integrally fixed to the mounting portion, said pressing portion extending upwardly from said mounting portion a height such that when said mounting portion is mounted inside the mouth on the teeth said pressing portion presses upwardly against at least one pressure point selected from the group consisting of Geikou, Biryu, Sanshou, Koryou, Kinshin, jaw articulation, and Gyokueki such that said pressing portion presses from inside the mouth at least one of said pressure points.

* * * * *